(12) United States Patent
Saxer et al.

(10) Patent No.: US 7,214,038 B2
(45) Date of Patent: May 8, 2007

(54) HOSE CARTRIDGE FOR A PERISTALTIC PUMP

(75) Inventors: Daniel Saxer, Zurich (CH); René Fässler, Zurich (CH); Stephan Michels, Dinhard (CH)

(73) Assignee: Ismatec SA, Glattbrugg (CH)

( * ) Notice: Subject to any disclaimer, the term of this patent is extended or adjusted under 35 U.S.C. 154(b) by 648 days.

(21) Appl. No.: 10/661,695

(22) Filed: Sep. 12, 2003

(65) Prior Publication Data

US 2004/0057856 A1 Mar. 25, 2004

(30) Foreign Application Priority Data

Sep. 23, 2002 (DE) .................. 102 44 090

(51) Int. Cl.
*F04B 43/12* (2006.01)
(52) U.S. Cl. ............................. 417/477.2; 417/477.11
(58) Field of Classification Search ............. 417/477.2, 417/477.9, 477.11
See application file for complete search history.

(56) References Cited

U.S. PATENT DOCUMENTS

| | | | | |
|---|---|---|---|---|
| 3,597,124 A | * | 8/1971 | Adams .................. | 417/477.11 |
| 4,187,057 A | * | 2/1980 | Xanthopoulos .......... | 417/477.2 |
| D264,134 S | * | 4/1982 | Xanthopoulos .......... | 417/477.2 |
| 4,886,431 A | * | 12/1989 | Soderquist et al. ....... | 417/477.2 |
| 5,257,917 A | * | 11/1993 | Minarik et al. .......... | 417/477.2 |
| 5,709,539 A | * | 1/1998 | Hammer et al. ........ | 417/477.11 |
| 5,752,813 A | * | 5/1998 | Tyner et al. ............. | 417/477.2 |
| 5,927,956 A | * | 7/1999 | Lim et al. ................ | 417/477.2 |
| 6,109,895 A | * | 8/2000 | Ray et al. ................ | 417/477.2 |
| 6,835,049 B2 | * | 12/2004 | Ray ........................ | 417/477.2 |

* cited by examiner

*Primary Examiner*—Michael Koczo, Jr.
(74) *Attorney, Agent, or Firm*—Tarolli, Sundheim, Covell & Tummino LLP

(57) ABSTRACT

A hose cartridge for a peristaltic pump comprises a cartridge housing provided with a lateral recess. The recess is delimited at least partially by an element having essentially the shape of a segment of a circle. A roller wheel of the peristaltic pump can engage that recess once the cartridge is attached to the peristaltic pump. The cartridge housing is provided with two support arms, and a groove extends from one of the support arms along three outer side faces of the cartridge housing to the other support arm. The ends of the support arms are provided each with a hose take-up member for retaining stoppers attached to a hose section. Such a hose cartridge is of very compact design ensures an easy handling.

8 Claims, 2 Drawing Sheets

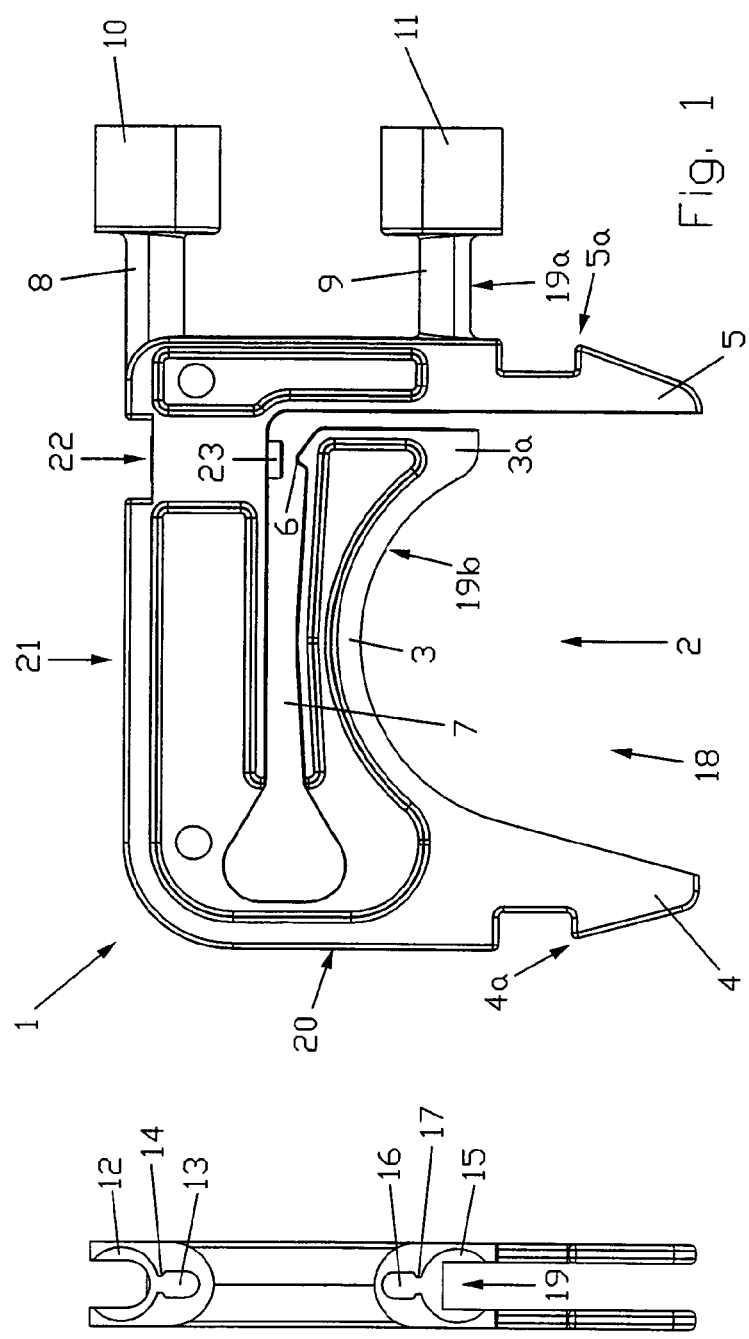
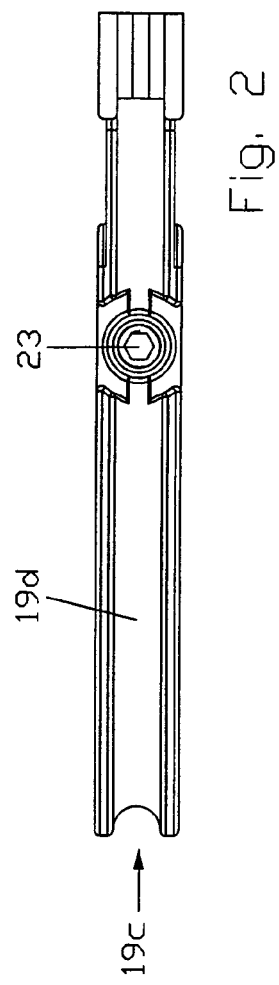

HOSE CARTRIDGE FOR A PERISTALTIC PUMP

BACKGROUND OF THE INVENTION

The present invention refers to a hose cartridge for a peristaltic pump equipped with a roller wheel and means for attaching the hose cartridge. The hose cartridge comprises a cartridge housing provided with a lateral recess. The recess is adapted to receive the roller wheel of the peristaltic pump when the hose cartridge is attached to the peristaltic pump. The cartridge housing is provided with means cooperating with the means for attaching the hose cartridge provided on the peristaltic pump.

By means of such a hose cartridge, it is to be ensured that a hose section containing the medium to be conveyed can be attached to the peristaltic pump easily and quickly. Since such hose cartridges are basically known in the prior art, in the following, only the characteristics of the hose cartridge are discussed that are relevant or related to the present invention.

In order to be in a position to fix the hose or hose section to a hose cartridge quickly, easily and with a defined bias, embodiments of hoses are known that are provided with two so-called stoppers. The distance between these two stoppers is standardized to a great extent and usually amounts to about 140 mm. Generally, it is not a problem to attach such a hose or hose section to a hose cartridge known in the prior art because those hose cartridges usually are of such a physically large dimension that the hose section can be attached to the cartridge with one stopper at one end of the cartridge and the other stopper at the other end of the cartridge.

PRIOR ART

The document EP 1,137,886 discloses a roller pump for peristaltically conveying a medium that is provided with a hose cartridge. The hose runs in longitudinal direction through the hose cartridge, i.e. it leaves the hose cartridge at the side opposite to the side where it enters the cartridge. The hose cartridge is attached to the roller pump by means of a lockable cover. As can be seen from the illustration in FIG. 1 of this document, such a cartridge has a relatively great length and, thus, needs a lot of space.

The document EP 1,108,891 discloses a hose cartridge for a peristaltic pump. The cartridge housing is provided with an opening for receiving the roller wheel of the peristaltic pump. This opening is delimited, at one side, by a U-shaped front portion whereby the hose rests on the inner side of this front portion. The hose itself is provided, at the one end, with a first stopper, designated as connection element, to be fixed to the cartridge housing by means of stop surfaces. The other end of the hose is provided with a further connection element movable along the hose between a mounting position and an operating position, whereby it also can be fixed in the latter position.

OBJECTS OF THE INVENTION

Since there is a trend, even in the field of peristaltic pumps, to design such apparatuses smaller and smaller, there is also a need and desire for a smaller hose cartridge. Thus, it is an object of the invention to provide a hose cartridge for a peristaltic pump which is considerably smaller than corresponding hose cartridges of the prior art. It is a further object of the invention to provide a hose cartridge for a peristaltic pump which can be used with standardized hoses having a distance between the stoppers that is quite great and initially designed for larger hose cartridges. It is a still further object of the invention to provide a hose cartridge for a peristaltic pump that can be attached to the peristaltic pump quickly and easily.

SUMMARY OF THE INVENTION

To meet these and other objects, the present invention provides a hose cartridge for a peristaltic pump equipped with a roller wheel and means for attaching the hose cartridge. The hose cartridge comprises a cartridge housing provided with a lateral recess, said recess being adapted to receive the roller wheel of the peristaltic pump when the hose cartridge is attached to the peristaltic pump. The recess is delimited at least partially by an element essentially having the shape of a segment of a circle and comprises a groove extending at least along a portion of the element for receiving a hose portion. The cartridge housing is provided with connecting means cooperating with the means for attaching the hose cartridge provided on the peristaltic pump.

The groove extending at least along a portion of the element for receiving a hose portion is extended to run along an outer face of the cartridge housing located opposite to the element essentially having the shape of a segment of a circle such that the hose section to be received by the groove leaves the cartridge housing at the same lateral face as it enters the cartridge housing.

Preferred embodiments of the hose cartridge according to the invention are described in the dependent claims 2 to 9.

BRIEF DESCRIPTION OF THE DRAWINGS

In the following, an embodiment of the apparatus according to the invention will be further described, with reference to the accompanying drawings, in which:

FIG. 1 shows a side view of the hose cartridge according to the invention;

FIG. 2 shows a top view of the hose cartridge of FIG. 1;

FIG. 3 shows a rear view of the hose cartridge of FIG. 1, and;

DETAILED DESCRIPTION OF A PREFERRED EMBODIMENT

Figure 4:
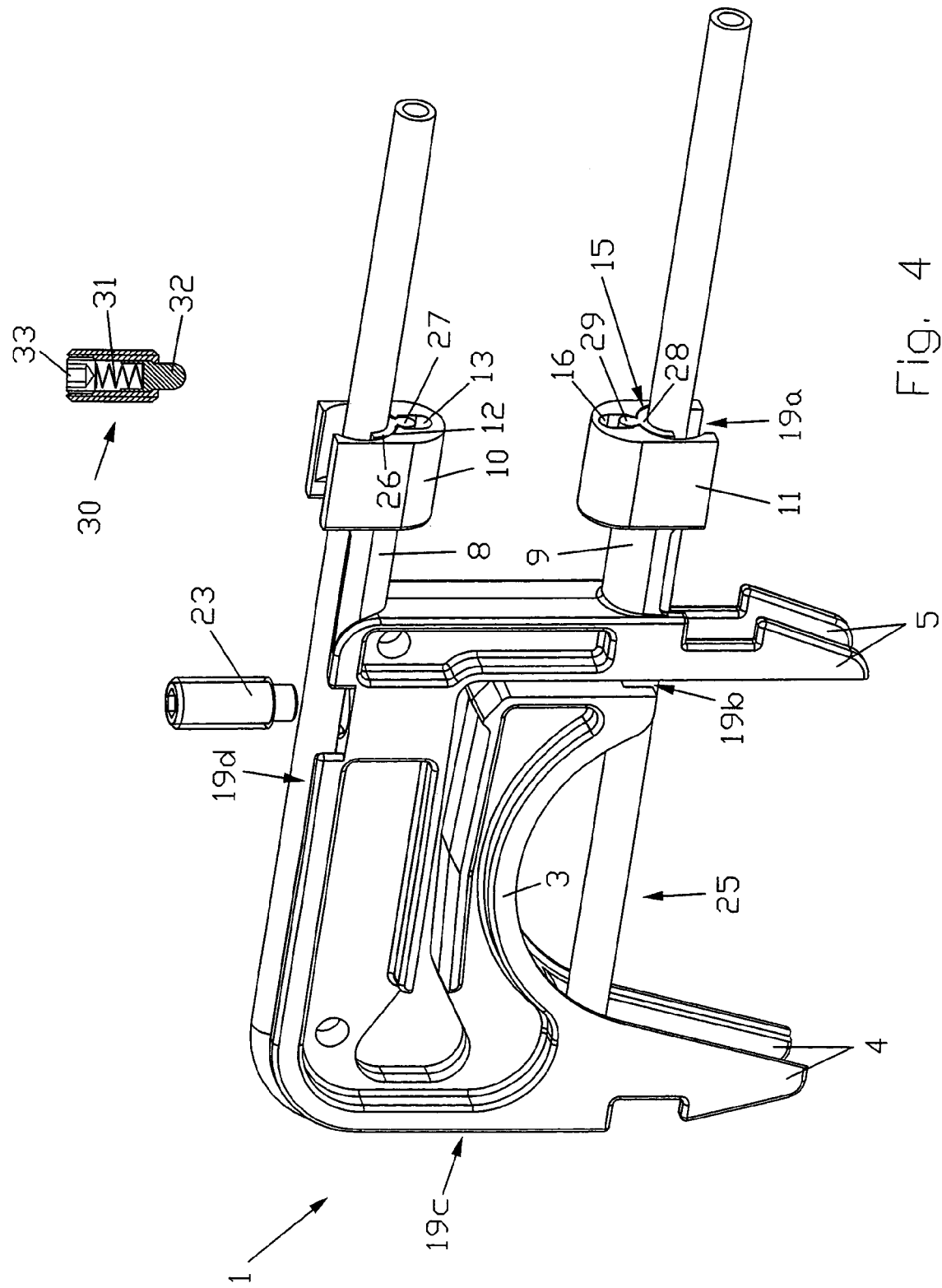
FIG. 4 shows a perspective view of the hose cartridge of FIG. 1, having a hose inserted therein.

The general design of an embodiment of the hose cartridge according to the present invention will be described in more detail with reference to FIGS. 1 to 3. The hose cartridge comprises a cartridge housing 1, provided with a lateral recess 2. An element or cantilever arm 3 having generally the shape of a segment of a circle delimits the inner side of this lateral recess 2. The cartridge housing 1 is provided with a slot 7 located between the cantilever arm 3 and the top portion of the cartridge housing 1. The cantilever arm 3 is attached to the cartridge housing only at one of its ends; thus, the cantilever arm is radially resilient, particularly in the region of its end portion 3a.

The bottom portion of the cartridge housing comprises two mounting means or two pairs of legs 4 and 5, whereby each leg is provided with a catch member 4a, 5a at its front end. The two pairs of legs 4, 5 delimit the afore mentioned recess 2 on both sides. Due to the fact that a slot 7 is provided in the cartridge housing 1, and further due to the fact that the cantilever arm 3 is fixed to the cartridge housing 1 only at one side of the arm 3, the two pairs of legs 4, 5 are resiliently movable towards each other as well, thus enabling a quick attachment of the cartridge housing 1 to a pump (not shown) or to corresponding protrusions thereof.

At the right side of the cartridge housing, as seen in FIG. 1, two support arms 8 and 9 are provided, each provided at its end with a hose take-up member 10, 11 having a greater diameter than the arms 8, 9. Both of the hose take-up members 10, 11 are provided each with a bigger and a smaller cutout 12, 13; 15, 16 adapted to receive each one of two two-part retaining members or stoppers 26, 28 provided on the hose section to be attached to the hose cartridge 1. It should be noted that the hose section to be attached to the cartridge housing 1 and the associated retaining members or stoppers 26, 28 of the hose are not shown in FIGS. 1 to 3.

FIG. 3 shows that the larger cutouts 12, 15 are of essentially circular cross section, while the smaller cutouts 13, 16 show an essentially oval cross section. Between the two cutouts 12, 13 and 15, 16, respectively, in each case a necking 14, 17 is provided, adapted to clampingly fix the associated retaining member or stopper 26, 28 of the hose section.

The major part of the outer periphery of the cartridge housing 1 is provided with a continuous groove 19, whereby the individual groove sections are designated by reference numerals 19a, 19b, 19c and 19d. The groove 19 serves for receiving a tube section, as will be explained in more detail herein after. The first groove section 19a extends from the hose take-up member 11 along the lower side of the lower support arm 9 and runs between the right pair of legs 5. The groove section extending along the lower side of the cantilever arm 3 is designated with reference numeral 19b. The groove section 19b runs between the left pair of legs 4 and opens into a groove section 19c, extending along the left outer side of front face 20 of the cartridge housing 1, opposite to the two support arms 8, 9, to the top of the cartridge housing 1. Therefrom, a groove section 19d extends along the top side of the cartridge housing 1 and along the top side of the support arm 8 through the hose take-up member 10. In simple words, the groove 19 runs along the three outer sides 18, 20 and 21 of the cartridge housing 1 from the lower support arm 9 to the upper support arm 8.

Moreover, the cartridge housing 1 is provided with a vertically extending threaded bore 22 adapted to receive a set screw 23. Opposite to the free end of the set screw 23, the cantilever arm 3 is provided with a cam 6. Thus, by screwing in the set screw 23 to a more or less extent, the deflection of the cantilever arm 3 can be limited once the hose cartridge is inserted in a peristaltic pump (not shown). Consequently, the pressure exerted onto the section 25 of the tube (FIG. 4) by the associated roller wheel of the peristaltic pump can be adjusted.

FIG. 4 shows a perspective view of the cartridge housing 1 together with a hose section 25 attached thereto. In the situation shown in FIG. 4, the hose section 25 is fixed in the hose take-up members 10, 11 of the support arms 8, 9 by means of two retaining members or stoppers 26, 28 attached to the hose section 25. In its rest position as shown in FIG. 4, the hose section 25 between the two pairs of legs 4, 5 runs along a straight line. It is understood, once the cartridge housing 1 is inserted into the peristaltic pump (not shown), the hose section 25 running between the two pairs of legs 4, 5 is pushed into the groove section 19b of the cantilever arm 3 by means of the roller wheel of the peristaltic pump.

Even if the cartridge housing 1 according to the present invention is of comparatively compact dimensions, the cartridge housing 1 comprises a groove 19 matches the widely used hoses provided with two retaining members or stoppers 26, 28 being relatively far from each other, with the result that these more or less standardized hoses can be used with a small and compact cartridge housing 1 for the first time.

In FIG. 4, it can be further seen that the retaining members or stoppers 26, 28 each comprise a radial protrusion 27, 29 received in the associated smaller cutout 13, 16 of the hose take-up members 10, 11 to ensure that the hose section 25 attached to the cartridge housing 1 cannot rotate. Moreover, it is evident from FIG. 4 that the hose section 25 enters and leaves the cartridge housing 1 at the same side.

In place of the previously mentioned set screw 23, for example a resiliently supported pin 30 can be provided. As shown in the cross sectional view thereof in FIG. 4, the pin 30 comprises a front portion 32 resting against a compression spring 31. Once inserted into the cartridge housing 1, the front portion 32 of the pin 30 rests against the cam 6 of the cantilever arm 3 to resiliently support it. The bias force can be adjusted by means of an adjustment screw 33. If such a resilient pin 30 is used in a cartridge housing 1, the cantilever arm 3 is resiliently pressed against the hose section 25 once the cartridge is inserted into a peristaltic pump (not shown).

In using the hose cartridge according to the present invention, the hose section can be easily attached thereto as follows: First, the one retaining member or stopper 28 is inserted into the larger cutout 15 of the hose take-up member 11. Then, the hose is guided around the cartridge housing 1 to be embedded in the groove 19 and stretched to such an extent that the second retaining member or stopper 26 can be inserted into the cutout 12 of the hose take-up member 10. As soon as the hose section 25 is released, the retaining member or stopper 26 is pulled into the cutout 12 of the hose take-up member 10.

The hose cartridge equipped with the hose section 25 can be quickly and easily attached to a peristaltic pump (not shown) or to matching protrusions thereof. Particularly, the roller wheel of the peristaltic pump can be laterally brought in contact with the hose cartridge through the lateral recess 2, thus avoiding the need to slide the hose cartridge over a central opening onto the roller wheel of the peristaltic pump, as is the case with most of the conventional hose cartridges.

Besides the fact that a hose cartridge according to the invention is of very compact dimensions, a further advantage may be seen in the fact that several hose cartridges may be attached and removed from a peristaltic pump parallely and independently of each other.

Due to the fact that both support arms 8, 9 are located at the same lateral side of the cartridge housing 1, the hose section is fed in and out at the same lateral side, too; thus, the physical size of the entire hose cartridge is further reduced.

What is claimed is:

1. A hose cartridge for a peristaltic pump equipped with a roller wheel, the hose cartridge comprising:

a cartridge housing provided with a lateral recess, said recess being adapted to receive said roller wheel of said peristaltic pump when said hose cartridge is attached to said peristaltic pump;

said recess being delimited at least partially by an element essentially having the shape of a segment of a circle and said element comprising a groove extending at least along a portion of said element for receiving a hose portion;

said cartridge housing being provided with mounting means cooperating with said peristaltic pump;

said groove extending at least along a portion of said element for receiving a hose portion being extended to run along an outer face of said cartridge housing located opposite to said element essentially having the shape of a segment of a circle such that the hose section to be received by said groove extends to said cartridge housing at the same side as it extends from said cartridge housing, three lateral faces of said cartridge housing are provided each with a groove section for constituting said groove receiving said hose section, whereby said side of said cartridge housing is provided with two support arms, the free end of each of said support arms being equipped with a hose take-up member for receiving and retaining fixing members or stoppers provided on said hose section.

2. A hose cartridge according to claim 1 in which each of said hose take-up members provided at the free ends of said support arms comprises two cutouts for receiving and retaining a two-part fixing member or stopper of said hose section.

3. A hose cartridge according to claim 2 in which a necking is provided between said two cutouts of said hose take-up members for clampingly fixing said fixing element or stopper of said hose section.

4. A hose cartridge for a peristaltic pump equipped with a roller wheel, the hose cartridge comprising:

a cartridge housing provided with a lateral recess, said recess being adapted to receive said roller wheel of said peristaltic pump when said hose cartridge is attached to said peristaltic pump;

said recess being delimited at least partially by an element essentially having the shape of a segment of a circle and said element comprising a groove extending at least along a portion of said element for receiving a hose portion;

said cartridge housing being provided with mounting means cooperating with said peristaltic pump;

said groove extending at least along a portion of said element for receiving a hose portion being extended to run along an outer face of said cartridge housing located opposite to said element essentially having the shape of a segment of a circle such that the hose section to be received by said groove extends to said cartridge housing at the same side as it extends from said cartridge housing, said element essentially having the shape of a segment of a circle is constituted by a cantilever arm resiliently attached to said cartridge housing.

5. A hose cartridge according of claim 4 in which at least two lateral faces of said cartridge housing are provided each with a groove section for constituting said groove receiving said hose section.

6. A hose cartridge according to claim 4 in which means are provided for delimiting the resilient deflection of said cantilever arm.

7. A hose cartridge for a peristaltic pump equipped with a roller wheel, the hose cartridge comprising:

a cartridge housing provided with a lateral recess, said recess being adapted to receive said roller wheel of said peristaltic pump when said hose cartridge is attached to said peristaltic pump;

said recess being delimited at least partially by an element essentially having the shape of a segment of a circle and said element comprising a groove extending at least along a portion of said element for receiving a hose portion;

said cartridge housing being provided with mounting means cooperating with said peristaltic pump;

said groove extending at least along a portion of said element for receiving a hose portion being extended to run along an outer face of said cartridge housing located opposite to said element essentially having the shape of a segment of a circle such that the hose section to be received by said groove extends to said cartridge housing at the same side as it extends from said cartridge housing, said mounting means comprises two pairs of legs, each of said leg pair being provided with at least one catch member.

8. A hose cartridge according to claim 7 in which said groove runs through said two pairs of legs, whereby said lateral recess provided in said cartridge housing is laterally delimited by said two pairs of legs.

* * * * *